Dec. 3, 1963 F. W. ANDERSON Plant Pat. 2,325
NECTARINE TREE
Filed Oct. 30, 1962
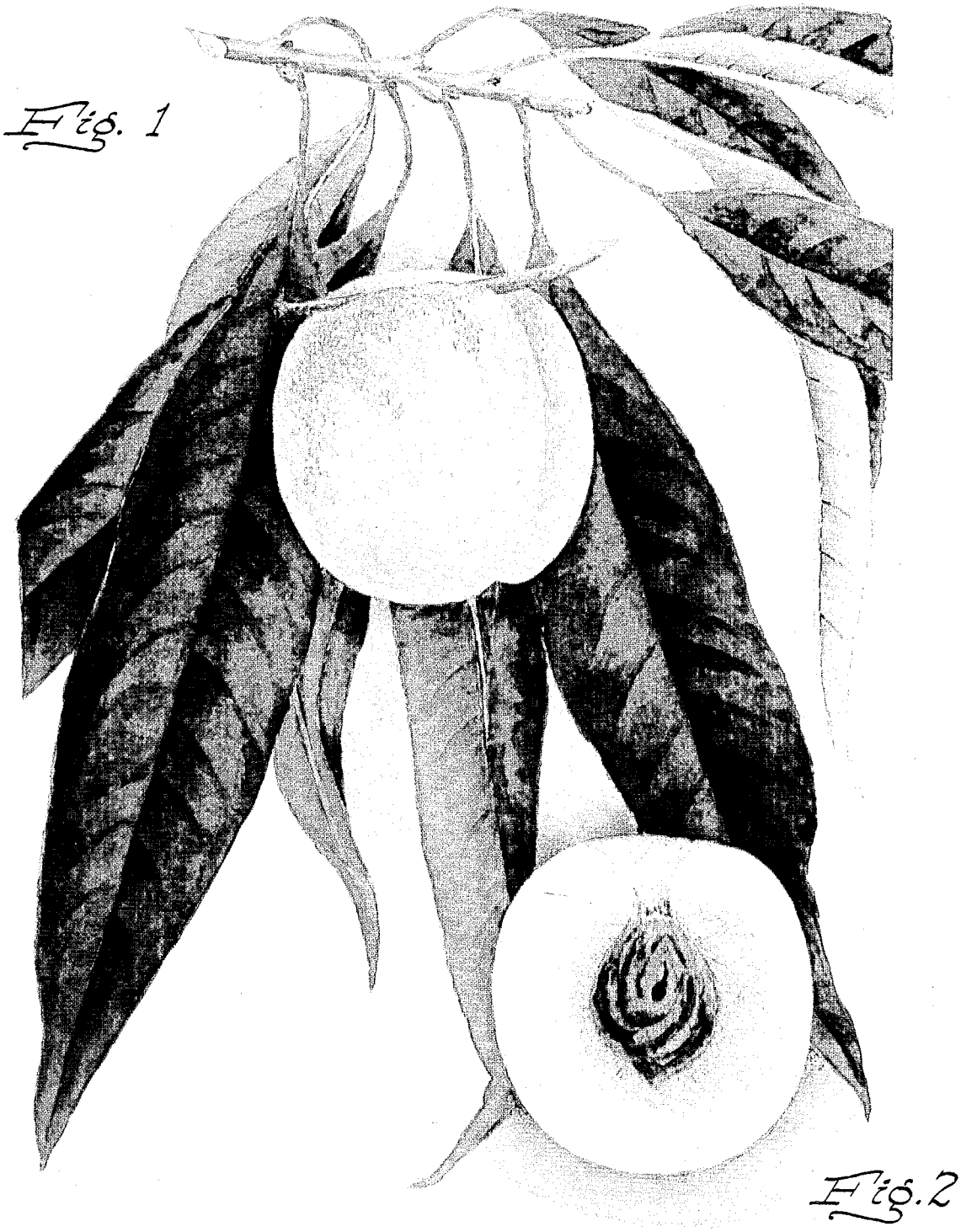
WITNESS
Addison J. Avery
INVENTOR
Frederic W. Anderson
Webster & Webster
ATTYS.

United States Patent Office

Plant Pat. 2,325
Patented Dec. 3, 1963

2,325
NECTARINE TREE

Frederic W. Anderson, Merced, Calif., assignor to L. E. Cooke Co., San Gabriel, Calif., a corporation Filed Oct. 30, 1962, Ser. No. 234,269
1 Claim. (Cl. Plt.—40)

This invention is directed to a new and distinct variety of nectarine tree which would fall within group 87 of the classification by Caillavet and Souty, entitled "Monographie des Principales Variétés de Pêchers," 1950 edition.

The present variety is principally characterized by its genetically small or dwarf-size tree having very short internodes, and the bearing—by such tree—of substantially normal size, white fleshed,, freestone fruit of acceptable quality. The variety, which is well adapted for growing both as an ornamental tree and for the production of fruit for home and local market use, is believed to be the first dwarf nectarine tree which bears white fleshed fruit.

The present variety of nectarine is a sib and is generally very similar to the Golden Prolific (United States Plant Patent No. 2,193), but—in comparison—is distinctively characterized by fruit which is white fleshed instead of yellow; is in harvest approximately ten days earlier; has more aroma; and is of better eating quality.

The variety was originated by me, in my experimental orchard located near Merced, California, during a long-term plant breeding project—spanning approximately ten years—which object was the origination of fruit trees, including nectarine trees, of such small or dwarf size that—in addition to ornamental value—pruning, thinning, and harvesting operations could be conducted without the use of ladders and by a person standing on the ground adjacent the tree.

The variety was originated by me, under close and careful observation, in the following manner:

The Flory dwarf peach (unpatented) was crossed with the Late Le Grand nectarine (United States Plant Patent No. 1,035), and the resultant seed all produced normal size peach trees which bore white fleshed peach fruit. In turn, seed from such trees produced about seventy-five percent normal size trees and twenty-five percent dwarf trees; some being peach trees and other nectarine trees. Of these last mentioned peach and nectarine trees, both those of normal and dwarf size, approximately three-fourths bore white fleshed fruit while the remaining one-fourth bore yellow fleshed fruit. The present variety is a selection of one of such dwarf nectarine trees whose fruit was white fleshed; the variety having been selected by me—for subsequent reproduction—upon the recognition of its commercial potential as a combination ornamental and fruit tree.

Subsequently, asexual reproduction of the variety was accomplished by me, in my experimental orchard located as aforesaid, by grafting on older nectarine trees; such reproductions having run true in all respects.

In the drawings:

FIG. 1 is an elevation showing one of the fruits, together with twigs and leaves.

FIG. 2 is a sectional elevation of one of the fruits, with the stone remaining in place.

Referring now specifically to this new and distinct variety of nectarine tree, the following is a detailed pomological description thereof in outline; all major color plate identification being by reference to Maerz and Paul Dictionary of Color, except where common terms of color definition are employed.

Tree:
- *Size.*—Dwarf. Average height—6–8 feet.
- *Vigor.*—Medium.
- *Form.*—Spreading.
- *Density.*—Dense to open.
- *Production.*—Productive.

Trunk: Size—stocky.

Branches:
- *Size.*—Stocky.
- *Texture.*—Shaggy.

Leaves:
- *Size.*—Medium. Average length—5½". Average width—15/16".
- *Margin.*—Crenate.
- *Petiole.*—Short; medium thickness.
- *Glands.*—Average number and position—two to three on petiole and two or more on base of blade. Alternate; medium size; reniform.
- *Color.*—Top side—medium green (22–L–8). Under side—lighter green (21–K–5).

Flower buds: Size—medium.

Flowers:
- *Blooming period.*—March 6 to March 20, 1962. Medium as compared with other varieties.
- *Size.*—Large.
- *Fertility.*—Self-fertile, with red anthers.

Fruit:
- *Maturity when described.*—Eating ripe—August 12, 1962.
- *Date of first picking.*—August 8, 1962.
- *Date of last picking.*—August 15, 1962.
- *Size.*—Uniform; large. Average diameter axially—2½". Average transversely in suture plane—2 7/16".
- *Form.*—Uniform; symmetrical; globose to slightly oblate.
- *Suture.*—Distinct; extends from base to apex.
- *Cavity.*—Circular. Average depth—5/16". Average breadth—¼". Markings—red mottling.
- *Base.*—Rounded.
- *Apex.*—Depressed.

Skin:
- *Thickness.*—Medium.
- *Texture.*—Medium.
- *Tendency to crack.*—None noted.
- *Down.*—Wanting.
- *Color.*—Pale yellow (9–H–1 to 9–D–2), partially mottled with red (3–L–10 to 4–K–9), shading to pink (2–F–9 to 2–K–9).

Flesh:
- *Texture.*—Soft.
- *Ripens.*—Even.
- *Flavor.*—Subacid to mild.
- *Eating quality.*—Fair to good.
- *Color.*—White with very pale greenish cast (17–C–1 to 17–C–2), with red (6–L–6 to 4–J–1) near stone. Surface of pit cavity—red.

Stone:
- *Type.*—Free.
- *Size.*—Medium. Average length—1¼". Average breath—1". Average thickness—13/16".
- *Tendency to split.*—Slight.
- *Color.*—Brown (8–L–12 to 56–L–12).
- *Kernels.*—Bitter.

Use: Home, and local market.

Keeping quality: Medium.

Shipping quality: Medium to poor; i.e., not firm enough for commercial long distance shipment.

The tree and its fruit herein described may vary in slight detail due to climatic and soil conditions under which this variety may be grown; the present description being of the variety as grown in the Central Valley of California.

The following is claimed:

A new and distinct variety of dwarf nectarine tree, as illustrated and described, which bears normal size freestone fruit having pale yellow skin mottled with red shading to pink; the tree and its fruit having general resemblance to the Golden Prolific (United States Plant Patent No. 2,193) but—in comparison—being distinctively characterized by fruit which is white fleshed instead of yellow; is in harvest approximately ten days earlier; has more aroma and is of better eating quality.

No references cited.